United States Patent
Bruggeman et al.

[11] Patent Number: 6,059,747
[45] Date of Patent: May 9, 2000

[54] SYRINGE PUMP INFUSION CONTROL SET

[75] Inventors: Paul J. Bruggeman, Dublin; Spencer W. Beaufore, Hilliard, both of Ohio

[73] Assignee: Medex, Inc., Hilliard, Ohio

[21] Appl. No.: 08/895,131

[22] Filed: Jul. 16, 1997

[51] Int. Cl.[7] .................................................. A61M 31/00
[52] U.S. Cl. ................................ 604/49; 604/247; 604/30
[58] Field of Search .................................. 604/49, 51, 53, 604/247, 248, 249, 183–186, 28, 30–33, 80, 83, 131

[56] References Cited

U.S. PATENT DOCUMENTS

| | | |
|---|---|---|
| 292,824 | 2/1884 | Kennedy . |
| 1,850,132 | 3/1932 | Morse . |
| 2,032,723 | 3/1936 | Schweser . |
| 2,485,842 | 10/1949 | Pennington . |
| 3,957,052 | 5/1976 | Topham . |
| 4,210,173 | 7/1980 | Choksi et al. . |
| 4,219,021 | 8/1980 | Fink . |
| 4,253,501 | 3/1981 | Ogle . |
| 4,921,488 | 5/1990 | Maitz et al. . |
| 5,002,528 | 3/1991 | Palestrant . |
| 5,176,658 | 1/1993 | Ranford . |
| 5,356,375 | 10/1994 | Higley . |
| 5,439,452 | 8/1995 | McCarty . |
| 5,807,312 | 9/1998 | Dzwonkiewicz . |

OTHER PUBLICATIONS

Medex, Inc., *MX815—Flush–N–Fill Rev. Jul. 13, 1992*.
Medex, Inc., *Duckbill Specifications* © *1996*.
Critical Care Products, *Safe–T–Care 92062–A*, Jan. 1994.

*Primary Examiner*—John D. Yasko
*Attorney, Agent, or Firm*—Wood, Herron & Evans, L.L.P

[57] ABSTRACT

A syringe pump infusion control set (10) includes a high cracking bottle port check valve (22) and a low cracking patient port check valve (50) by which to selectively and automatically couple a syringe (40) to the fluid source (36) and the patient (58) with proper dynamic response for an injection from the syringe (40).

15 Claims, 1 Drawing Sheet

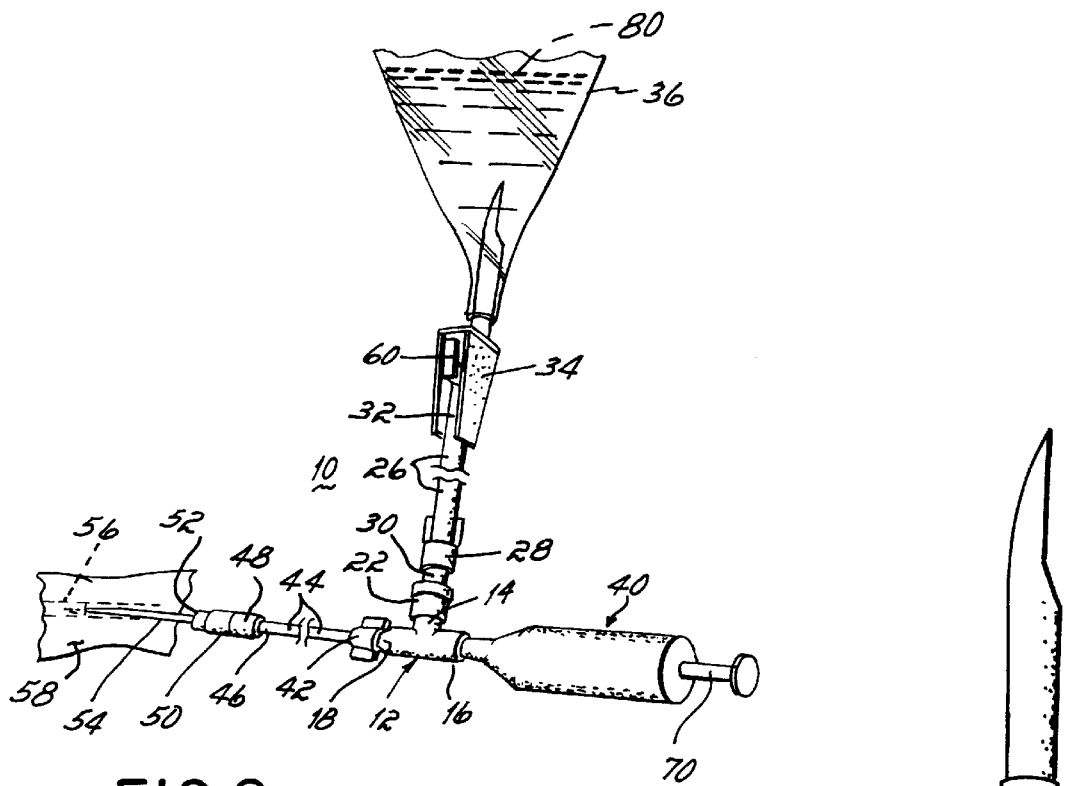
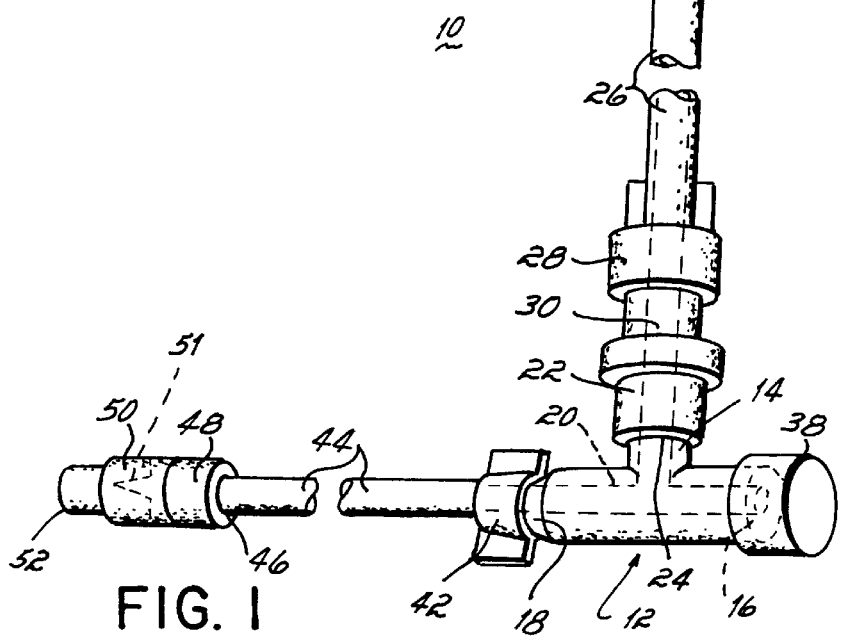
FIG. 2
FIG. 1

SYRINGE PUMP INFUSION CONTROL SET

BACKGROUND OF THE INVENTION

I. Field of the Invention

The present invention relates to infusion control sets for use with a syringe pump or the like.

II. Description of Prior Art

A syringe pump infusion control set may include a three port stopcock by which to selectively connect a bolus injection syringe (such as part of a syringe pump device) to either a bulk source of fluid or a patient. The syringe is coupled to one stopcock port ("syringe port") with a bulk fluid reservoir such as a bottle or bag of medicine coupled to another port thereof ("bottle port" or "supply port") via a length of tubing. The third port ("patient port") is coupled to another tube to connect to a catheter or the like inserted into a patient's circulatory system.

The stopcock normally has at least two positions. In one position, the syringe port is coupled to the bottle port so as to permit filling of the syringe with the medicine from the fluid source. The other position of the stopcock couples the syringe port to the patient port so as to permit controlled infusion of the medicine from the syringe or other pump to the patient. In this way, small boluses of medicine may be administered to the patient under control of the syringe while maintaining a bulk supply of fluid available for refilling the syringe without opening the system to atmosphere such as by removing the syringe or catheter from the fluidic system connected to the patient. To avoid the risk of the bulk source of fluid coupling, directly to the patient, the stopcock may have a limited range of motion such that the bottle port is never fluidically coupled directly to the patient port.

While the stopcock-based sets have the advantage of allowing the syringe to be refilled and used for bolus injections without disconnection of the system, there is the disadvantage of requiring manipulation of the stopcock for proper use. To overcome that disadvantage, it has been proposed to replace the stopcock with an automatically-responding junction device having normally closed, high cracking valves forming an integral part of each of the bottle and patient ports. The valved junction has the advantage that actuation of the syringe either to fill or inject automatically opens and closes the respective valves to accomplish the proper port selectivity. Thus, pulling on the syringe plunger creates a high negative pressure within the junction causing the bottle port valve to open while the patient port valve is held closed so as to allow the syringe to be filled without fluid communication between the bulk fluid source and the patient. Similarly, pushing the syringe plunger in to inject the medicine creates a large positive pressure within the junction against which the bottle port valve remains closed and the patient port valve is forced open to thus inject the medicine into the patient, all without allowing the bottle port to be fluidically coupled directly to the patient port.

While the valved junction syringe pump system is thus easier to use than the stopcock-based system, there are certain drawbacks associated with the valved junction as compared to the stopcock-based system. In particular, with the valved junction, the dynamic response of the system to actuation of the syringe plunger for an injection is less than desirable. By way of example, there is a short period of delay before the patient port valve opens resulting in delayed delivery of the medicine to the patient with possible adverse consequences.

SUMMARY OF THE INVENTION

The present invention provides an improved syringe pump infusion control set which provides the automatic functioning of the valved junction but without the delayed delivery found to be associated with the valved junction. In this regard, high cracking valves typically associated with the junction require a large pressure build-up before they will open. It is found that compliance of the syringe and tubing adversely affects the ability to create the desired pressure build-up resulting in the undesirable delay in opening of the patient port valve after actuation of the syringe. This delay becomes especially significant at low rates such as between 0.01 Ml/hour and 1.0 Ml/hour. Yet, the high cracking valves have the advantage that they will not open under slight pressures (such as a gravity drip) so as to maintain necessary fluid isolation between the bulk source and the patient. To this end, and in accordance with the principles of the present invention, it is found that the dynamic response is improved and yet leakage is prevented by replacing the valve associated with the patient port with a low cracking valve whereas the bottle port valve is retained as a high cracking valve.

By virtue of the foregoing, there is thus provided an improved syringe pump infusion control set that incorporates the advantageous features of the valved junction without the attendant dynamic response delay.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

FIG. 1 is a perspective view of a syringe pump infusion control set in accordance with the principles of the present invention, and FIG. 2 is a schematic view of a syringe pump infusion control set in use with a source of fluid supply and coupled to a patient catheter for purposes of describing operation of the invention.

DETAILED DESCRIPTION OF THE DRAWINGS

With reference to FIG. 1, there is shown a syringe pump infusion control set 10 constructed in accordance with the principles of the present invention. Set 10 includes a T-shaped coupling junction 12 having three ports 14, 16, and 18 each in constant fluid communication with one another via the internal T-shaped fluid passageway 20 (shown in dotted line) extending therebetween. A high cracking, normally closed check valve 22 is attached at its outlet side 24 to bottle or supply port 14 exteriorly of junction 12. A source conduit 26, such as a 30 inch length of medical grade, frosted 0.145" O.D. tubing, is coupled at its proximal end 28 to the inlet side 30 of valve 22, with the distal end 32 of tubing 26 coupled to spike 34 for attachment to a bulk source or reservoir of fluid 36 (FIG. 2) such as an IV bottle or bag of medicine.

The second or syringe port 16 of junction 12 has a port protector 38 attached thereto to protect from touch contamination during set up. When set 10 is in use as will be described in greater detail below, port protector 38 is replaced with a delivery device such as a syringe 40 (FIG. 2) attached to port 16 by which to selectively apply negative pressure or inject fluid from port 16 for purposes to be hereinafter described.

The third or patient port 18 of junction 12 is coupled to the proximal end 42 of a patient conduit 44, such as 60 inch length of 0.078" O.D. tubing. The distal end 46 of tube 44 is coupled to the inlet side 48 of a low cracking, normally closed check valve 50. The outlet side 52 of valve 50 provides a standard male Luer lock connector by which to couple directly to a catheter or the like 54 (FIG. 2) or other connector (not shown) coupled into the circulatory system 56 of a patient 58.

Valve 22 is a high cracking valve such that it will not open until the opening or cracking pressure (in this case negative pressure at outlet side 24) equals or exceeds a threshold pressure. Importantly, the cracking pressure of valve 22 should be high enough such that it will remain closed under typical head height pressure. In this regard, the cracking pressure may be in the range of between about 66 mmHg (millimeters mercury) and about 750 mmHg. The range is more advantageously between about 77 mmHg and about 259 mmHg. Valve 22 may be a 5N02-B100-CM40 valve available from NP Medical, Inc. of Clinton, Mass., with a cracking pressure of about 155 mmHg. Moreover, valve 22 must have a sufficiently high back pressure withstand that it will not open in response to an overpressure from syringe 40 (e.g., 45 psi). As a consequence, valve 22 will not open in response to the low pressure at which valve 50 will open as will be discussed and instead will remain closed to thereby isolate supply 36 from patient port 18 during an injection.

Valve 50, on the other hand, is selected to open at very low pressure such that valve 50 may be considered as almost open at atmospheric pressure. In this regard, valve 50 will open once the opening or cracking pressure (in this case positive pressure at inlet side 48) equals or exceeds a threshold pressure which is well below the typical head height pressure. In this regard, the cracking pressure of valve 50 may be in the range of between about 0 in $H_2O$ (inches water) and about 25 in $H_2O$. The range is more advantageously between about 0 in $H_2O$ and about 12 in $H_2O$. Valve 50 may be a 0.078" tubing port/MLL mini duck bill valve (having a duck-bill septum 51 therein as shown in dotted line) available from Medex, Inc., of Columbus, Ohio, the assignee hereof (part no. B1745-06) with a cracking pressure of about 6 in $H_2O$ (about 11 mmHg). Thus, with valve 50, actuation of syringe 40 for an injection will almost immediately create a sufficient positive pressure within junction 12 and conduit 44 to open valve 50 without the delay of a high cracking valve and the attendant consequences thereof, yet at a pressure insufficient to overcome the back pressure withstand of valve 22. By the same token, negative pressure within junction 12 tends to hold valve 50 closed so that opening of valve 22 for filling of syringe 40 will continue to isolate supply 36 from patient 58 downstream of valve 50.

In use, and with reference to FIG. 2, spike 34 is inserted into the fluid supply bag or bottle 36. If supply 36 is a flexible bag such as a plastic IV bag, then spike 34 may be unvented. If source 36 is a glass bottle or other less flexible housing, then spike 34 should be vented such as by opening the vent port 60 provided therewith as is well known in the art. Port protector 38 is removed from port 16 and a syringe 40 (which may be manually operable but is advantageously a machine operable pumped device) is attached to port 16. Finally, the outlet side 52 of valve 50 is coupled to a catheter 54 connected to the patient 58 such as to the patient's blood circulatory system within blood vessel 56. When syringe 40 is to be filled, the operator withdraws the plunger 70 thereof to apply a negative pressure at port 16. That negative pressure is coupled through passageway 20 to cause valve 22 to open and draw fluid 80 from source 36 down source conduit 26, into and through valve 22, port 14, and port 16, up into syringe 40. The negative pressure also couples down patient conduit 44 to valve 50 which is held closed in the presence of that negative pressure.

After syringe 40 is filled to the desired level, plunger 70 is actuated (manually or automatically) to inject the fluid 80 therein back into port 16. The positive pressure of the injecting fluid into passageway 20 is communicated to valve 22 which is normally closed in the presence of that pressure such that fluid injected into port 16 flows out of port 18 and down patient conduit 44 whereupon the build-up of positive pressure promptly opens valve 50 and holds it open to thereby allow the fluid 80 to pass promptly and smoothly into patient 58 via catheter 54. The cracking pressure of valve 50 is sufficiently low as above-discussed as to provide the desired dynamic response for the injection such that even drip fluid from port 16 can also hold valve 50 open by the positive pressure of gravity, all without opening valve 22 to thus maintain isolation between patient 58 and source 36.

By virtue of the foregoing, there is thus provided a syringe pump infusion control set which has a desirable dynamic response for delivery of medication from syringe 40 while automatically providing the necessary selectivity of coupling between the syringe, bottle and patient ports.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, while placement of valve 50 distally from junction 12 may have advantageous anti-retrograde properties, valve 50 could be connected directly at port 18. Also, valve 22 and/or 50 are shown as valves separate from junction 12 and attached thereto. Valve 22 and/or 50 could alternatively be built integrally into junction 12. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A syringe pump infusion control set comprising:

a coupling junction having a bottle port, a patient port, and a syringe port;

a normally closed, high cracking valve having an inlet side and an outlet side and being operable in response to negative high cracking pressure at the outlet side, the high cracking valve outlet side being coupled to the bottle port;

a low cracking valve having an inlet side and an outlet side and being held open in response to positive low cracking pressure at the inlet side, the low cracking valve inlet side being coupled to the patient port; and the syringe port of the junction being adapted to couple to a syringe by which to selectively apply negative high cracking pressure and positive low cracking pressure at the syringe port whereby application of negative high cracking pressure at the syringe port draws fluid at the inlet side of the high cracking valve into the syringe while the low cracking valve remains closed and application of positive low cracking pressure at the syringe port injects fluid from the syringe to the outlet side of the low cracking valve while the high cracking valve remains closed.

2. The syringe pump infusion control set of claim 1 further comprising:

a source conduit coupled to the inlet side of the high cracking valve; and a spike coupled to the source conduit adapted to fluidically engage with a fluid reservoir whereby to supply fluid to the high cracking valve inlet side.

3. The syringe pump infusion control set of claim 1 further comprising:

a patient conduit having a proximal end and a distal end, the patient conduit being coupled at its proximal end to the patient port and at its distal end to the inlet side of the low cracking valve.

4. The syringe pump infusion control set of claim 1 wherein the low cracking valve includes a duckbill septum.

5. The syringe pump infusion control set of claim 1 wherein the high cracking valve has a cracking pressure above a typical head height pressure.

6. The syringe pump infusion control set of claim 1 wherein the high cracking valve has a cracking pressure of between about 66 mmHg and about 750 mmHg.

7. The syringe pump infusion control set of claim 1 wherein the high cracking valve has a cracking pressure of between about 77 mmHg and about 259 mmHg.

8. The syringe pump infusion control set of claim 1 wherein the high cracking valve has a cracking pressure of about 155 mmHg.

9. The syringe pump infusion control set of claim 1 wherein the low cracking valve has a cracking pressure well below a typical head height pressure.

10. The syringe pump infusion control set of claim 1 wherein the low cracking valve has a cracking pressure of between about 0 inH$_2$O and about 25 inH$_2$O.

11. The syringe pump infusion control set of claim 1 wherein the low cracking valve has a cracking pressure of between about 0 inH$_2$O and about 12 inH$_2$O.

12. The syringe pump infusion control set of claim 1 wherein the low cracking valve has a cracking pressure of about 6 inH$_2$O.

13. The syringe pump infusion control set of claim 1 further comprising a syringe coupled to the syringe port by which to selectively apply said cracking pressures.

14. A method of syringe pump infusion comprising:

coupling a source of fluid to a junction via a high cracking valve adapted to open in response to a negative high cracking pressure;

coupling a patient to the junction via a low cracking valve adapted to open in response to a positive low cracking pressure;

filling a syringe with fluid from the source through the junction by application of a negative high cracking pressure from the syringe;

injecting the fluid from the syringe to the patient by application of a positive low cracking pressure from the syringe.

15. A method of syringe pump infusion comprising:

fluidically coupling a source of fluid to a syringe in response to a high cracking pressure while fluidically uncoupling the source of fluid from a patient in the presence of said high cracking pressure;

fluidically coupling the syringe to the patient in response to a low cracking pressure while fluidically uncoupling the source of fluid from the patient in the presence of said low cracking pressure.

\* \* \* \* \*